US009997269B2

(12) United States Patent
Roh et al.

(10) Patent No.: US 9,997,269 B2
(45) Date of Patent: Jun. 12, 2018

(54) METHODS OF TRACING REGIONS OF INTEREST, RADIOGRAPHIC APPARATUSES, METHODS OF CONTROLLING THE RADIOGRAPHIC APPARATUSES, AND RADIOGRAPHY METHODS

(71) Applicant: Samsung Electronics Co., Ltd., Suwon-Si, Gyeonggi-Do (KR)

(72) Inventors: Kyung Shik Roh, Seongnam-si (KR); Seung Yong Hyung, Yongin-si (KR); Ji Yeun Kim, Seoul (KR); Jong Won Lee, Uiwang-si (KR); Ju Suk Lee, Hwaseong-si (KR); Won Jun Hwang, Seoul (KR); Hyo Seok Hwang, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 679 days.

(21) Appl. No.: 14/533,873

(22) Filed: Nov. 5, 2014

(65) Prior Publication Data

US 2015/0206614 A1    Jul. 23, 2015

(30) Foreign Application Priority Data

Jan. 20, 2014 (KR) .................. 10-2014-0006672

(51) Int. Cl.
*H05G 1/10* (2006.01)
*G01N 23/04* (2018.01)
(Continued)

(52) U.S. Cl.
CPC ............... *G21K 5/10* (2013.01); *A61B 6/405* (2013.01); *A61B 6/4441* (2013.01); *A61B 6/482* (2013.01);
(Continued)

(58) Field of Classification Search
CPC ......... A61B 6/06; A61B 6/405; A61B 6/4441; A61B 6/461; A61B 6/482; A61B 6/504;
(Continued)

(56) References Cited

U.S. PATENT DOCUMENTS 7,340,033 B2* 3/2008 Mollus .................. A61B 6/06
378/147
8,681,941 B2* 3/2014 Bernhardt ............. A61B 6/542
378/97
(Continued)

FOREIGN PATENT DOCUMENTS

DE    10 2012 205 238    10/2012
DE    10 2011 083 876    4/2013
(Continued)

OTHER PUBLICATIONS

Jun. 18, 2015 Extended European Search Report issued in corresponding European Application No. 15151454.4-1660.
Navab, Nassir et al. "Camera Augmented Mobile C-Arm (CAMC): Calibration, Accurary Study, and Clinical Applications." 29.7 (2010): 1412-423.
(Continued)

*Primary Examiner* — Irakli Kiknadze
(74) *Attorney, Agent, or Firm* — Harness, Dickey & Pierce, P.L.C.

(57) ABSTRACT

A radiographic apparatus may comprise: a radiation irradiating module configured to irradiate radiation to an object; and/or a processing module configured to automatically set a part of a region to which the radiation irradiating module is able to irradiate the radiation, to a region of interest, and further configured to determine at least one of a radiation irradiation position and a radiation irradiation zone of the radiation irradiating module based on the region of interest.

10 Claims, 18 Drawing Sheets

(51) Int. Cl.
*G21K 5/10* (2006.01)
*A61B 6/00* (2006.01)
*A61B 6/06* (2006.01)

(52) U.S. Cl.
CPC ............ *A61B 6/504* (2013.01); *A61B 6/5217* (2013.01); *A61B 6/542* (2013.01); *G01N 23/04* (2013.01); *A61B 6/06* (2013.01); *A61B 6/461* (2013.01)

(58) Field of Classification Search
CPC ....... A61B 6/5217; A61B 6/542; A61B 6/505; A61B 6/583; A61B 2560/02; A61B 2562/0238; A61B 2576/00; A61B 2576/026; A61B 5/0035; A61B 5/0042; A61B 5/0075; A61B 5/0555; A61B 5/1455; A61B 5/14556; A61B 5/4064; A61B 5/7203; G01N 23/04; G01N 21/07; G01N 21/253; G21K 5/10; G11B 2007/0013; G11B 7/00736; G11B 7/1267; G11B 7/24038
USPC ..................................... 378/8, 20, 62, 64, 95
See application file for complete search history.

(56) References Cited

U.S. PATENT DOCUMENTS

| 2009/0062641 | A1  | 3/2009 | Barbu et al. |
| 2013/0101084 | A1* | 4/2013 | Shimizu ................ A61B 6/022 378/42 |
| 2014/0112438 | A1* | 4/2014 | Mountney ............... A61B 6/12 378/62 |

FOREIGN PATENT DOCUMENTS

| DE | 10 2012 201 798 | 8/2013 |
| JP | 2003-284716 A | 10/2003 |
| JP | 2011156348 A | 8/2011 |
| WO | WO-2012-123850 A1 | 9/2012 |
| WO | WO-2013/169814 A1 | 11/2013 |

OTHER PUBLICATIONS

Office Action from corresponding European Patent Application 15151454.1, dated Apr. 10, 2017.
Japanese Office Action dated Dec. 19, 2017 issued in corresponding Japanese Application No. 2014-245043 (with translation).

* cited by examiner

METHODS OF TRACING REGIONS OF INTEREST, RADIOGRAPHIC APPARATUSES, METHODS OF CONTROLLING THE RADIOGRAPHIC APPARATUSES, AND RADIOGRAPHY METHODS

CROSS-REFERENCE TO RELATED APPLICATION(S)

This application claims priority from Korean Patent Application No. 10-2014-0006672, filed on Jan. 20, 2014, in the Korean Intellectual Property Office (KIPO), the entire contents of which are incorporated herein by reference.

BACKGROUND

1. Field

Some example embodiments of the present disclosure may relate generally to methods of tracing regions of interest, radiographic apparatuses, methods of controlling radiographic apparatuses, and/or radiography methods.

2. Description of Related Art

A radiographic apparatus may be an imaging system for acquiring images about the inside structure or tissue of an object using radiation. The radiographic apparatus may irradiate X-rays to an object, such as a human body or baggage, and/or may receive radiation transmitted through the object, thereby acquiring an image about the inside of the object. The radiographic apparatus may be widely used in various industrial fields such as the medical industry, since it can show the inside structure of an object without having to destroy the object. Examples of the radiographic apparatus may include digital radiography (DR), fluoroscopy, cardiography, computed tomography (CT), and mammography.

SUMMARY

Some example embodiments of the present disclosure may provide methods of tracing regions of interest (ROI), radiographic apparatuses, methods of controlling radiographic apparatuses, and/or radiography methods, capable of quickly and accurately setting and tracing an ROI.

In some example embodiments, a radiographic apparatus may comprise: a radiation irradiating module configured to irradiate radiation to an object; and/or a processing module configured to automatically set a part of a region to which the radiation irradiating module is able to irradiate the radiation, to a region of interest, and further configured to determine at least one of a radiation irradiation position and a radiation irradiation zone of the radiation irradiating module based on the region of interest.

In some example embodiments, the radiation irradiating module may irradiate radiation to the object according to the at least one of the radiation irradiation position and the radiation irradiation zone.

In some example embodiments, the radiographic apparatus may further comprise: a radiation detecting module configured to receive the radiation transmitted through the object. The processing module may be further configured to produce a radiographic image of the region of interest that corresponds to the radiation received by the radiation detecting module.

In some example embodiments, the processing module may be further configured to combine the radiographic image of the region of interest with a radiographic image acquired in advance to produce a combined radiographic image.

In some example embodiments, the radiographic apparatus may further comprise: a radiography module driver configured to move the radiation irradiating module.

In some example embodiments, the radiography module driver may be further configured to move the radiation irradiating module according to the radiation irradiation position.

In some example embodiments, the radiography module driver may comprise a C-arm module including the radiation irradiating module.

In some example embodiments, the radiation irradiating module may comprise an irradiation zone adjustor configured to block a part of the irradiated radiation, thereby adjusting at least one of the radiation irradiation position and the radiation irradiation zone.

In some example embodiments, the irradiation zone adjustor may be driven according to at least one of the radiation irradiation position and the radiation irradiation zone.

In some example embodiments, the radiation irradiating module may be further configured to move according to at least one of the radiation irradiation position and the radiation irradiation zone. The irradiation zone adjustor may be driven at a same time as or at a different time from when the radiation irradiating module moves.

In some example embodiments, the irradiation zone adjustor may comprise: a blocking element configured to block the irradiated radiation; and/or a blocking element driver configured to drive the blocking element.

In some example embodiments, the processing module may be further configured to automatically set the region of interest whenever the radiation irradiating module irradiates radiation. The processing module may be further configured to determine the at least one of the radiation irradiation position and the radiation irradiation zone of the radiation irradiating module whenever the region of interest is automatically set.

In some example embodiments, the processing module may be further configured to determine the at least one of the radiation irradiation position and the radiation irradiation zone of the radiation irradiating module at regular time intervals.

In some example embodiments, the processing module may be further configured to estimate a new region of interest based on a region of interest set in advance. The processing module may be further configured to determine the at least one of the radiation irradiation position and the radiation irradiation zone of the radiation irradiating module based on the new region of interest.

In some example embodiments, the processing module may be further configured to automatically set a part of the produced radiographic image to the region of interest using Kalman filtering.

In some example embodiments, a control method of a radiographic apparatus may comprise: automatically setting a part of a region, to which radiation is to be irradiated, to a region of interest; determining at least one of a radiation irradiation position and a radiation irradiation zone based on the region of interest; and/or performing radiography according to the at least one of the radiation irradiation position and the radiation irradiation zone to acquire a radiographic image of the region of interest.

In some example embodiments, the control method may further comprise: combining the radiographic image of the region of interest with a radiographic image acquired in advance to produce a combined radiographic image.

In some example embodiments, the control method may further comprise: controlling a radiation irradiating module of irradiating radiation based on the at least one of the radiation irradiation position and the radiation irradiation zone.

In some example embodiments, the controlling of the radiation irradiating module may comprise at least one of: moving the radiation irradiating module of irradiating radiation to an object based on the at least one of the radiation irradiation position and the radiation irradiation zone; and blocking a part of the irradiated radiation based on the at least one of the radiation irradiation position and the radiation irradiation zone to adjust the at least one of the radiation irradiation position and the radiation irradiation zone.

In some example embodiments, the moving of the radiation irradiating module and the adjusting of the at least one of the radiation irradiation position and the radiation irradiation zone may be performed at a same time or at different times.

In some example embodiments, a radiographic apparatus may comprise: a radiation irradiating module configured to irradiate radiation to an object; a radiation detecting module configured to receive the radiation from the radiation irradiating module via the object; and/or a processing module configured to set a region of interest of the radiation and to determine at least one of a radiation irradiation position and a radiation irradiation zone based on the region of interest.

In some example embodiments, the radiation irradiating module may irradiate radiation to the object according to the at least one of the radiation irradiation position and the radiation irradiation zone.

In some example embodiments, the processing module may be further configured to produce a radiographic image of the region of interest that corresponds to the radiation received by the radiation detecting module.

In some example embodiments, the processing module may be further configured to combine the radiographic image of the region of interest with a radiographic image acquired in advance to produce a combined radiographic image.

In some example embodiments, the radiographic apparatus may further comprise: a radiography module driver configured to move the radiation irradiating module.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
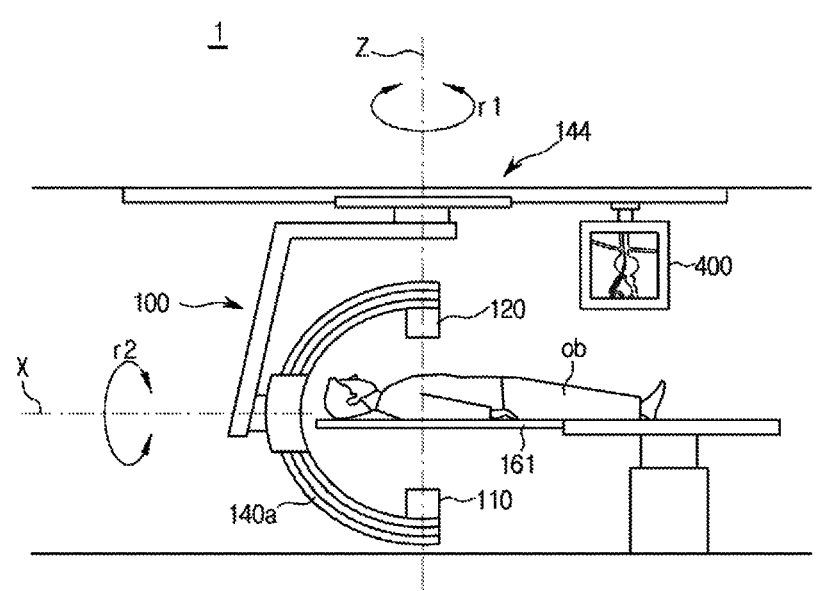
FIG. 1 is a view for describing a radiographic apparatus according to some example embodiments of the present disclosure.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 2:
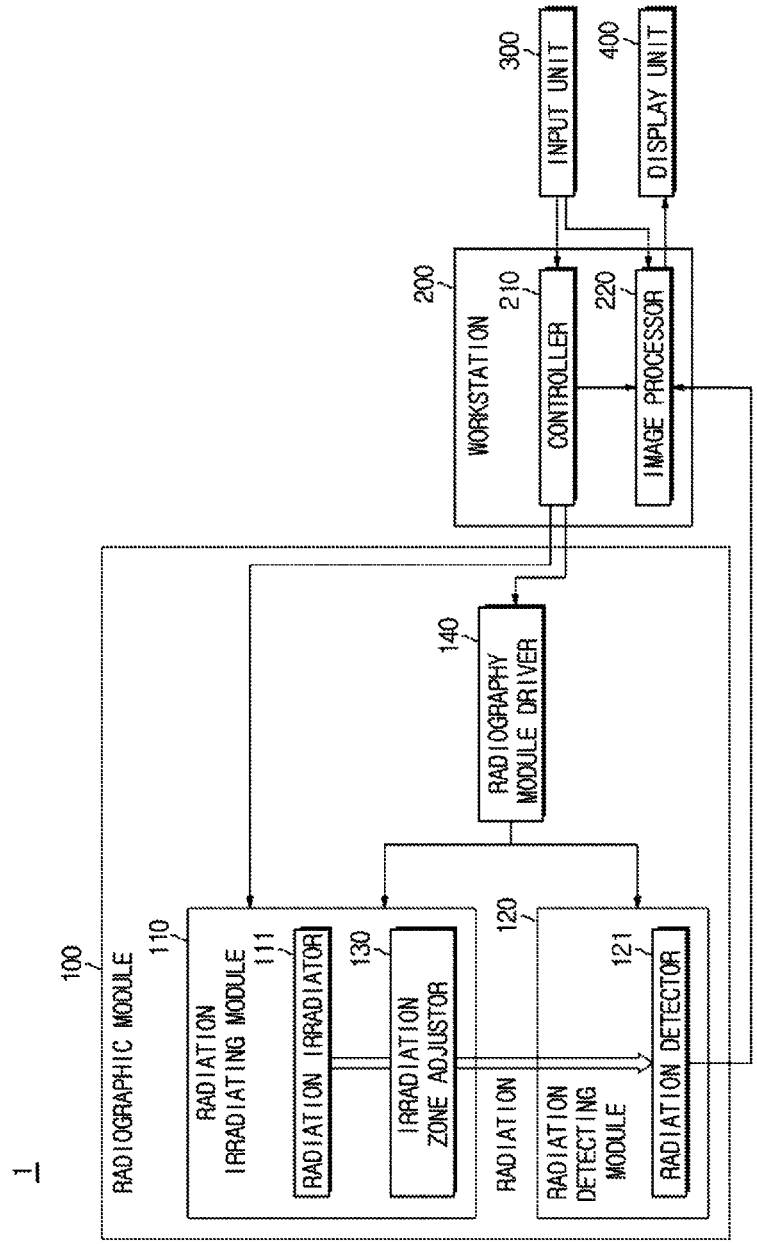
FIG. 2 is a block diagram illustrating a configuration of a radiographic apparatus according to some example embodiments of the present disclosure.

FIG. 1 is a view for describing a radiographic apparatus according to some example embodiments of the present disclosure, and FIG. 2 is a block diagram illustrating a configuration of a radiographic apparatus according to some example embodiments of the present disclosure.

As shown in FIGS. 1 and 2, a radiographic apparatus 1 may include a radiographic module 100. The radiographic module 100 may photograph an internal material, tissue, structure, etc. of an object ob using radiation of desired energy (that may or may not be predetermined). The object ob that is scanned by the radiographic module 100 may be a living thing, such as a human body or an animal, or a nonliving thing, such as baggage, a machine tool, or an architecture.

The radiographic module 100 may image the inside tissues of the object ob using the fact that different tissues in the object ob have different attenuation coefficients obtained by digitizing degrees to which the respective tissues absorb or transmit radiation. The differences between the attenuation coefficients of the different tissues may be caused by the properties (for example, densities) of the inside tissues of the object ob. Meanwhile, the same tissue may have different attenuation coefficients when different energy spectrums of radiation are applied thereto.

The intensity I of radiation transmitted through a desired tissue (that may or may not be predetermined) of the object ob may be expressed as Equation (1), below.

$$I = I_0 e^{-\mu t}, \tag{1}$$

where $I_0$ represents the intensity of radiation irradiated from the radiographic module 100, $\mu$ represents an attenuation coefficient according to the properties of the desired tissue (that may or may not be predetermined) of the object ob, and t represents the thickness of the desired tissue (that may or may not be predetermined) through which the radiation has been transmitted.

When radiography is performed, a desired contrast agent (that may or may not be predetermined) may be put into the object ob. A contrast agent is an agent that is put into a human body or an animal during radiography in order to increase the contrast of an inside material, for example, a specific tissue or blood vessels so that the inside material can be distinguished from the other tissues. The contrast agent may function to increase or decrease a degree to which the inside material of the object ob transmits radiation, so as to increase or decrease an attenuation coefficient of the material into which the contrast agent is put, thereby increasing a contrast between the material into which the contrast agent is put and other materials around that material. Therefore, when a contrast agent is used, a living body structure can be better understood, and lesions, etc. can be more clearly distinguished from other tissues, which enables a diagnostician to more easily and accurately diagnose a patient. One kind of contrast agent or a plurality of kinds of contrast agents may be put into the object ob, as necessary. The contrast agent may be Iodine, Iodine-Gadolinium, or $BaSO_4$. Also, the contrast agent may be gas, such as carbon dioxide ($CO_2$).

The radiographic module 100 may include a radiation irradiating module 110 and a radiation detecting module 120 for radiography, as shown in FIGS. 1 and 2. The radiation irradiating module 110 may irradiate radiation toward the object ob. The radiation detecting module 120 may receive radiation irradiated from the radiation irradiating module 110 and then transmitted through the object ob, and convert the received radiation into electrical signals so as to acquire a radiographic image.

The radiation irradiating module 110 and the radiation detecting module 120 may be movable. For example, the radiation irradiating module 110 and the radiation detecting module 120 may move linearly or in a curved manner. Also, the radiation irradiating module 110 and the radiation detecting module 120 may rotate with respect to a desired axis (that may or may not be predetermined), for example, an x-axis or z-axis of FIG. 1.

As shown in FIG. 1, the radiation irradiating module 110 and the radiation detecting module 120 may rotate in various directions (r1 and r2) with respect to an object ob who lies on a cradle 161. In this case, if the object ob is a human body, the radiation irradiating module 110 and the radiation detecting module 120 may rotate (r2) with respect to an x-axis extending from the head of the human body to the foot of the human body.

Also, the radiation irradiating module 110 and the radiation detecting module 120 may move linearly along the object ob. For example, the radiation irradiating module 110 and the radiation detecting module 120 may move along a desired axis (that may or may not be predetermined), for example, along the x-axis or z-axis of FIG. 1. If the object ob is a human body, the radiation irradiating module 110 and the radiation detecting module 120 may move in a direction from the head of the human body to the foot of the human body or in the opposite direction.

The radiation irradiating module 110 and the radiation detecting module 120 may be driven by a radiography module driver 140 (see FIG. 2) to move or rotate in a desired direction (that may or may not be predetermined). The radiography module driver 140 may include a plurality of drivers. The plurality of drivers may rotate or horizontally/vertically move the radiation irradiating module 110 and the radiation detecting module 120.

Figure 3:
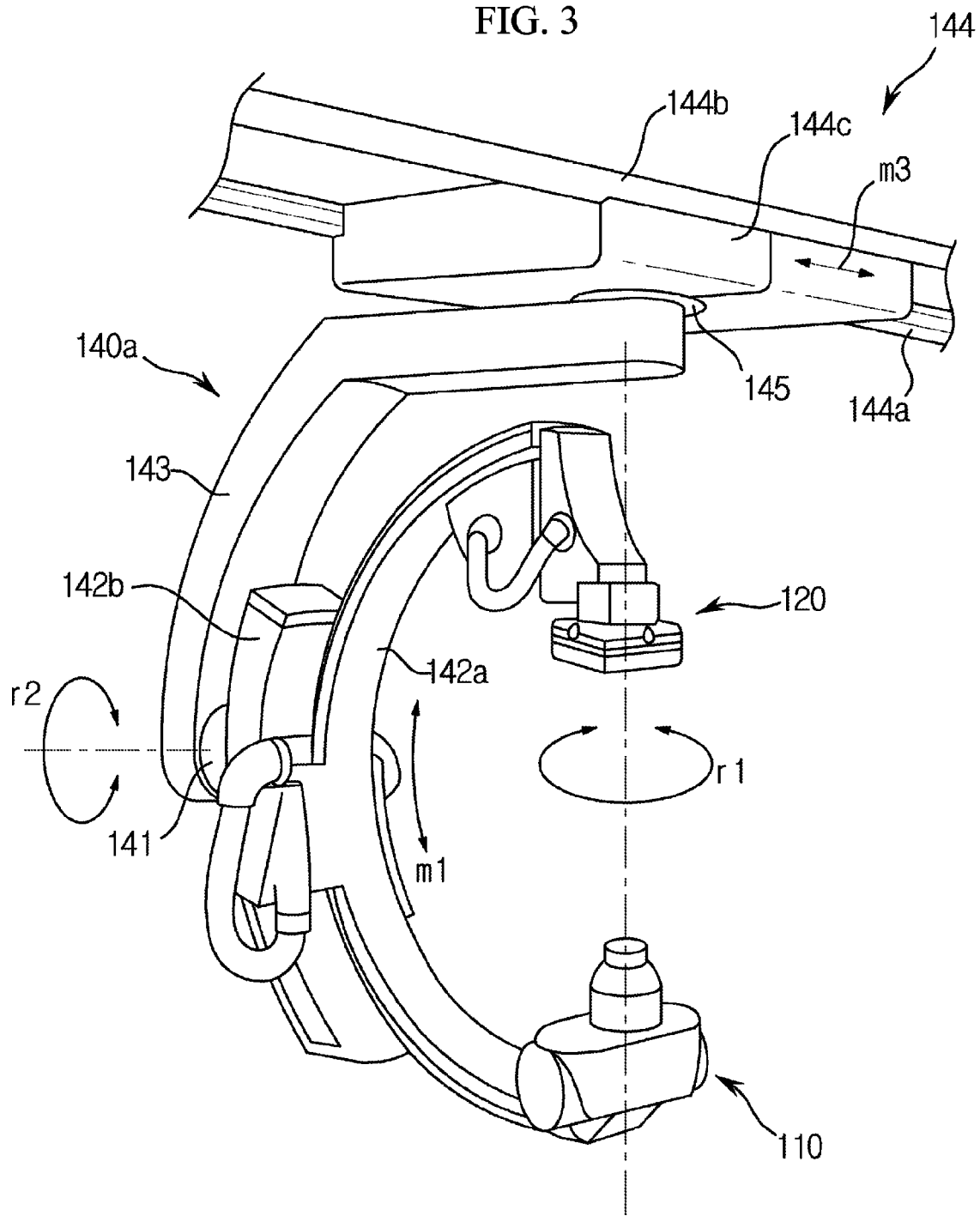
FIG. 3 is a perspective view of a radiographic module according to some example embodiments of the present disclosure.

FIG. 3 is a perspective view of the radiographic module 100 according to some example embodiments of the present disclosure.

According to some example embodiments, the radiography module driver 140 may be a C-arm module 140a as shown in FIGS. 1 and 3. The radiation irradiating module 110 and the radiation detecting module 120 may be installed in the C-arm module 140a.

The C-arm module 140a may include a first frame 142a curved in a 'C' shape, a second frame 142b coupled with the first frame 142a, a first rotating unit 141 to rotate the first frame 142a and the second frame 142b in a desired direction (that may or may not be predetermined), a third frame 143 with which the first rotating unit 141 is coupled, a second rotating unit 145 to rotate the third frame 143 with respect to a desired axis (that may or may not be predetermined), and a horizontal movement unit 144 with which the second rotating unit 145 is coupled. The radiation irradiating module 110 and the radiation detecting module 120 may be coupled with the first frame 142a at both ends of the first frame 142a in such a manner that the radiation irradiating module 110 and the radiation detecting module 120 face each other.

The second frame 142b may connect the first frame 142a to the first rotating unit 141, and enable the first frame 142a to move along a desired path m1 (that may or may not be predetermined). For example, the second frame 142b may include a rolling element. The rolling element may be a ball or a roller. The first rotating unit 141 may include a rail corresponding to the rolling element of the second frame 142b. In this case, the rolling element of the second frame 142b may move in a desired direction (that may or may not be predetermined) along the rail formed on the first rotating unit 141. If the rolling element moves, the second frame 142b may move to correspond to the movement of the rolling element. Since the second frame 142b is coupled with the first frame 142a, the first frame 142a may also move according to the movement of the second frame 142b. As a result, the radiation irradiating module 110 and the radiation detecting module 120 may also move along the desired path m1 (that may or may not be predetermined). According to some example embodiments, the second frame 142b may include a rail, and the first rotating unit 141 may include a rolling element. However, a designer may apply any other means for moving the first frame 142a along the desired path m1 (that may or may not be predetermined) relative to the second frame 142b and the first rotating unit 141.

The first rotating unit 141 may rotate (r2) with respect to a desired axis (that may or may not be predetermined) such that the first frame 142a and the second frame 142b rotate (r2) with respect to the desired axis (that may or may not be predetermined). The radiation irradiating module 110 and the radiation detecting module 120 may also rotate with respect to the desired axis (that may or may not be predetermined) according to the rotation of the first frame 142a and the second frame 142b. The first rotating unit 141 may include a rotatory element or a shaft element. The radiation irradiating module 110 may irradiate radiation to the object ob at various angles through the first frame 142a, the second frame 142b, and the first rotating unit 141. The radiation detecting module 120 may also receive radiation irradiated at various angles.

The first rotating unit 141 and the second rotating unit 145 may be rotatably connected to the third frame 143. The second rotating unit 145 may rotate (r1) the third frame 143 with respect to a desired axis (that may or may not be predetermined). When the third frame 143 rotates (r1) with respect to the desired axis (that may or may not be predetermined), the first frame 142a and the second frame 142b may also rotate (r1) with respect to the desired axis (that may or may not be predetermined). Since the third frame 143 can be rotated by the second rotating unit 145, the radiation irradiating module 110 and the radiation detecting module 120 may move along a desired path m3 (that may or may not be predetermined) regardless of the position of the object ob. The second rotating unit 145 may be connected to the horizontal movement unit 144.

The horizontal movement unit 144 may enable the radiation irradiating module 110 and the radiation detecting module 120 to move along the desired path m3 (that may or may not be predetermined). The horizontal movement unit 144 may slide on rails 144a and 144b. A housing 144c of the horizontal movement unit 144 may include rollers (not shown) so that the horizontal movement unit 144 can move when the rollers move along the rails 144a and 144b. Accordingly, the first frame 142a and the second frame 142b connected to the horizontal movement unit 144 through the third frame 143 may move along the desired path m3 (that may or may not be predetermined) according to the movement of the horizontal movement unit 144 and, as a result, the radiation irradiating module 110 and the radiation detecting module 120 may also move along the desired path m3 (that may or may not be predetermined) according to the movement of the horizontal movement unit 144.

The radiation irradiating module 110 may irradiate radiation to the object ob at various positions and at various angles by the C-arm module 140a, and the radiation detecting module 120 may receive radiation irradiated at various positions and at various angles. Accordingly, it is possible to acquire radiographic images at various positions about the object ob.

According to some example embodiments, the radiation irradiating module 110 may include a radiation irradiator 111 and an irradiation zone adjustor 130, as shown in FIG. 2. The radiation irradiator 111 may generate radiation of a desired energy spectrum (that may or may not be predetermined), and irradiate the radiation to the object ob. According to some example embodiments, the radiation irradiator 111 may generate radiation of a plurality of different energy spectrums, and irradiate the radiation to the object ob. Also, the radiation irradiator 111 may irradiate radiation to the object ob several times. According to some example embodiments, the radiation irradiator 111 may generate and irradiate radiation of the same energy spectrum or radiation of different energy spectrums, for several irradiations. If a plurality of contrast agents are put into the object ob, the radiation irradiator 111 may irradiate radiation of a plurality of different energy spectrums, according to the number of the contrast agents, to the object ob. According to some example embodiments, the radiation irradiator 111 may irradiate radiation of a monochromatic energy spectrum or radiation of a polychromatic energy spectrum to the object ob.

Figure 4:
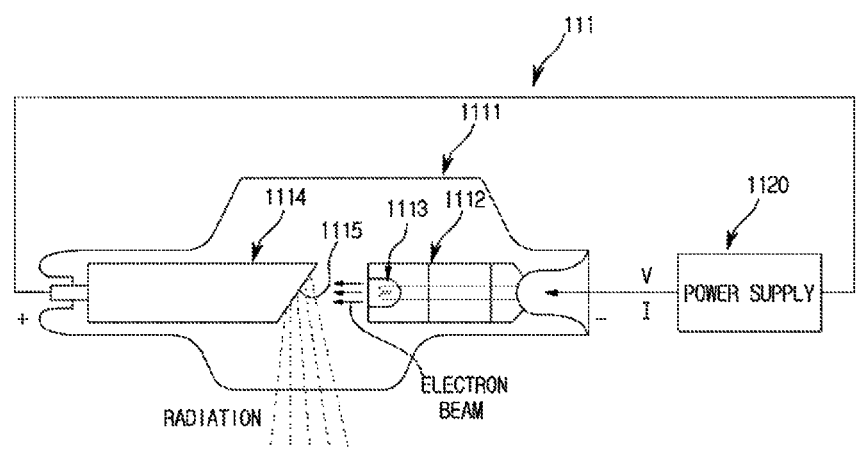
FIG. 4 is a view for describing a radiation irradiator according to some example embodiments of the present disclosure.

FIG. 4 is a view for describing the radiation irradiator 111 according to some example embodiments of the present disclosure.

As shown in FIG. 4, the radiation irradiator 111 may include a radiation tube to generate radiation, and a power supply 1120 to apply a current caused by a desired voltage (that may or may not be predetermined) to the radiation tube. According to an embodiment, the radiation irradiator 111 may include a plurality of radiation tubes. If the radiation irradiator 111 includes a plurality of radiation tubes, the respective radiation tubes may generate radiation of different energy spectrums. In detail, the radiation tube may include a tube body 1111, a cathode 1112, and an anode 1114.

The tube body 1111 may accommodate various elements, such as the cathode 1112 and the anode 1114, required to generate radiation, and stably fix the cathode 1112 and the anode 1114. Also, the tube body 1111 may seal the cathode 1112 to prevent electrons generated from the cathode 1112 from leaking out. A degree of vacuum in the tube body 1111 may be maintained at a high level of 10 mmHg to 7 mmHg. The tube body 1111 may be a glass tube made of silica (hard) glass.

The cathode 1112 may irradiate an electron beam ELECTRON BEAM consisting of a plurality of electrons according to a current I caused by a desired voltage V (that may or may not be predetermined) applied from the power source 1120, electrically connected to the cathode 1112, toward the anode 1114. In detail, the cathode 1112 may include a filament 1113 on which electrons are focused. The filament 1113 of the cathode 1112 may be heated according to a tube voltage applied from the power supply 1120 so as to emit electrons inside the tube body 1111. The electrons emitted from the filament 1113 may be accelerated inside the tube body 1111 to move toward to the anode 1114. Energy of the electrons emitted inside the tube body 1111 may depend on the tube voltage. The filament 1113 of the cathode 1112 may be made of a metal such as tungsten (W). According to some example embodiments, the cathode 1112 may include, instead of the filament 1113, a carbon nanotube.

The anode 1114 may generate desired radiation (that may or may not be predetermined). The anode 1114 may include a target 1115 with which electrons collide. The energy of electrons moving toward the anode 1114 may be sharply reduced when the electrons collide with the target 1115 formed on the anode 1114 and, at this time, radiation of energy corresponding to the applied tube voltage may be generated from the anode 1114, according to the law of conservation of energy. The anode 1114 may be made of a metal such as copper (Cu), and the target 1115 may be made of a metal, such as tungsten (W), chromium (Cr), iron (Fe), or nickel (Ni).

According to some example embodiments, the anode 1114 may be a stationary anode cut at a desired cutting angle (that may or may not be predetermined). In this case, the target 1115 may be formed on the cut part of the stationary anode 1114. According to some example embodiments, the anode 1114 may be a rotating anode having a rotatable, circular plate shape. One end of the rotating anode may be cut at a desired angle (that may or may not be predetermined), and the target 1115 may be formed on the cut part of the end of the rotating anode, like the stationary anode. Since the rotating anode has a higher rate of heat accumulation and a smaller focal spot size than the stationary anode, the rotating anode may be used to acquire more clear radiographic images.

The power supply 1120 may apply a current I, caused by a desired voltage V (that may or may not be predetermined), to the anode 1114 and the cathode 1112 in the tube body 1111. A potential difference between the anode filament 1113 and the anode 1114 in the tube body 1111 is called a tube voltage, and a current flowing by electrons collided with the anode 1114 is called a tube current. As the tube voltage increases, the velocity of electrons increases, resulting in an increase in energy of generated radiation. As the tube current increases, a dose of radiation may increase. Accordingly, by adjusting the voltage V and current I that are applied from the power supply 1120, the energy spectrum and dose of radiation that is irradiated may be adjusted.

Radiation irradiated from the radiation irradiator 111 may pass through the irradiation zone adjustor 130 (see FIG. 2), and then reach the object ob as shown in FIG. 1. The irradiation zone adjustor 130 may adjust an irradiation position and an irradiation zone of radiation irradiated from the radiation irradiator 111. More specifically, the irradiation zone adjustor 130 may block the entire or a part of the irradiated radiation to thereby adjust an irradiation position or an irradiation zone of the radiation. As a result, the irradiation zone adjustor 130 may adjust a position at which and a zone over which radiation is incident into the object ob.

Figure 5:
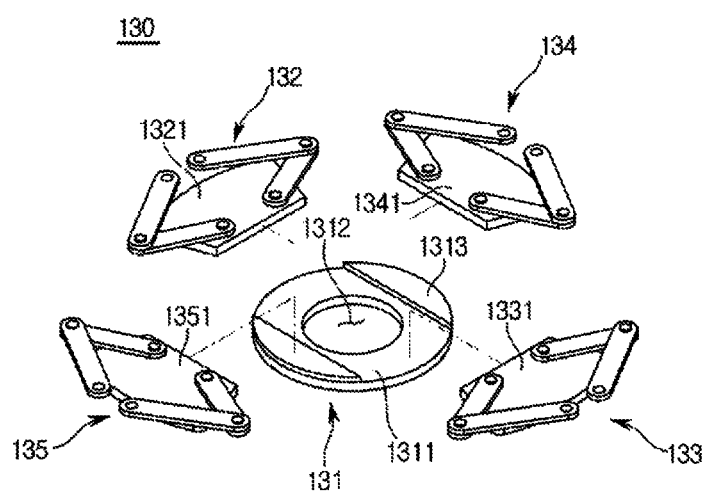
FIG. 5 is a perspective view of an irradiation zone adjustor according to some example embodiments of the present disclosure.
Figure 6:
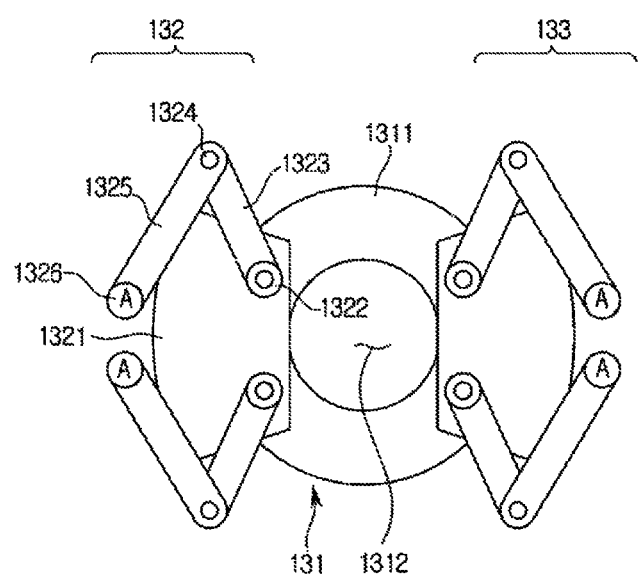
FIG. 6 is a top view of an irradiation zone adjustor according to some example embodiments of the present disclosure.

FIG. 5 is a perspective view of the irradiation zone adjustor 130 according to some example embodiments of the present disclosure, and FIG. 6 is a top view of the irradiation zone adjustor 130 according to some example embodiments of the present disclosure.

Referring to FIG. 5, the irradiation zone adjustor 130 may include a first collimator 131 and a plurality of blocking units 132 to 135. The first collimator 131 may filter the entire or a part of radiation that is irradiated from the radiation irradiator 111 (see FIG. 4) to irradiate radiation over a desired zone (that may or may not be predetermined) and in a desired direction (that may or may not be predetermined). The first collimator 131 may be disposed on an irradiation path of radiation that is irradiated from the radiation irradiator 111. The first collimator 131 may include a blocking plate 1311. The blocking plate 1311 of the first collimator 131 may be positioned at right angles to an irradiation direction of radiation. However, the position of the blocking plate 1311 is not limited to this. The blocking plate 1311 may be made of lead (Pb). An opening 1312 may be formed in a part of the blocking plate 1311. A part of radiation that is incident to the blocking plate 1311, among radiation irradiated from the radiation irradiator 111, may be absorbed or reflected so as to not reach the object ob. That is, radiation passing through the opening 1312 can reach the object ob. Accordingly, since a part of radiation irradiated from the radiation irradiator 111 can pass through the first collimator 131, an irradiation amount and an irradiation zone of radiation that is incident to the object ob may be adjusted.

Also, the first collimator 131 may further include a rest unit 1313 on which the blocking units 132 to 135 can be rested. The rest unit 1313 may be formed on one side of the blocking plate 1311. The rest unit 1313 may be formed on the upper surface of the blocking plate 1311. The rest unit 1313 may be a part of the blocking plate 1311, like parts on which the first blocking unit 132 and the second blocking unit 133 are rested, as shown in FIG. 5. According to some example embodiments, the rest unit 1313 may be protruded from the blocking plate 1311, like parts on which the third blocking unit 134 and the fourth blocking unit 135 are rested, as shown in FIG. 5. According to some example embodiments, the rest unit 1313 may be dents in the blocking plate 1311.

The blocking units 132 to 135 may absorb or reflect radiation so that a part of radiation irradiated from the radiation irradiator 111 can be incident to the object ob. By blocking radiation using the blocking units 132 to 135, a blocking zone of radiation may be adjusted. As a result, the blocking units 132 to 135 may adjust an irradiation position and an irradiation zone of radiation.

As shown in FIGS. 5 and 6, the blocking units 132 to 135 may include blocking element drivers 1322 to 1326 to move the respective blocking elements 1321, 1331, 1341, and 1351. The blocking elements 1321, 1331, 1341, and 1351 may absorb or reflect irradiated radiation to thereby block the radiation, or the blocking elements 1321, 1331, 1341, and 1351 may filter irradiated radiation to lower the intensity of the radiation. Each of the blocking elements 1321, 1331, 1341, and 1351 may be in a shape of a plane plate, as shown in FIG. 5. The blocking elements 1321, 1331, 1341, and 1351 may be made of lead (Pb) capable of absorbing radiation.

The blocking element drivers 1322 to 1326 may function to move each of the blocking elements 1321, 1331, 1341, and 1351. The blocking element drivers 1322 to 1326 may include a first coupling part 1322 coupled with the blocking element 1321, a first link part 1323 coupled with the first coupling part 1322 and rotating with respect to the first coupling part 1322, a second coupling part 1324 connecting the first link part 1323 to a second link part 1325 such that the first link part 1323 and the second link part 1325 rotate with respect to each other, the second link part 1325 coupled with the second coupling part 1324, and an actuator 1326 coupled with the second link part 1325 and driving the blocking element drivers 1322 to 1326. The actuator 1326, the first coupling part 1322, and the second coupling part 1324 may include a transmission device such as a motor.

If a control signal is received from a controller 210 (see FIG. 2), the transmission devices of the actuator 1326, the first coupling part 1322, and the second coupling part 1324 may start operating so that the actuator 1326, the first coupling part 1322, and the second coupling part 1324 can rotate or move. According to the operations of the transmission devices of the actuator 1326, the first coupling part 1322, and the second coupling part 1324, the first and second link parts 1323 and 1325 may move so that the blocking element 1321 moves accordingly. Then, the moved blocking element 1321 may be positioned to block a region of the opening 1312 of the first collimator 131. As a result, the blocking element 1321 may block a part of radiation irradiated from the radiation irradiator 111 to pass the other part of the radiation through the opening 1312 of the first collimator 131, thereby adjusting an irradiation position and an irradiation zone of radiation.

Figure 7:
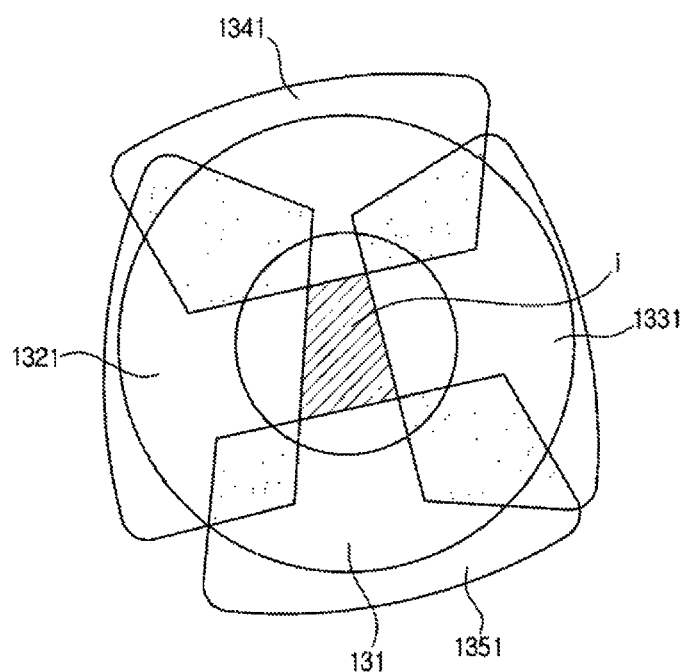
FIG. 7 is a view for describing a region of interest (ROI)

FIG. 7 is a view for describing an ROI.

For example, as shown in FIG. 7, the blocking elements 1321, 1331, 1341, and 1351 may block a region of the opening 1312 of the first collimator 131 so as to pass radiation though the region i of the opening 1312. In this case, radiation passed through the region i may be incident to the object ob so that an radiographic image corresponding to the region i can be acquired. Accordingly, by controlling the blocking units 132 to 135, a radiographic image for a desired region (that may or may not be predetermined), for example, an ROI may be acquired. Also, by controlling the blocking units 132 to 135 to change a region that is not blocked by the blocking elements 1321, 1331, 1341, and 1351, various radiographic images may be acquired. In other words, radiographic images for different ROIs may be acquired.

The blocking units 132 to 135 may be controlled in real time. Therefore, it is possible to change an ROI and acquire a radiographic image for the ROI in real time by controlling the blocking units 132 to 135 during radiography.

FIGS. 8 to 12 are views for describing methods of setting an ROI, according to some example embodiments of the present disclosure.

Radiographic images 0 shown in FIGS. 8 to 12 are images that can be acquired when the blocking units 132 to 135 do not block any of irradiated radiation. If the blocking units 132 to 135 are controlled to block, except for desired first, second, and third regions i1, i2, and i3 (that may or may not be predetermined) that are ROIs, the remaining regions, radiographic images for the first, second, and third regions i1, i2, and i3 may be acquired.

Figure 8:
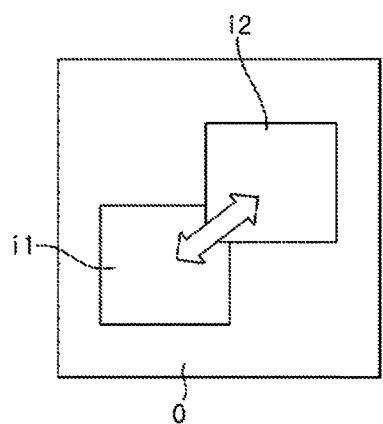
FIGS. 8 to 12 are views for describing methods of setting an ROI according to some example embodiments of the present disclosure.

In FIG. 8, an example of moving an ROI according to movement of a target of interest, for example, a surgical tool such as a catheter, inside an object ob, is shown. If a target of interest is located in a specific region (for example, the first region i1) of a radiographic image, the first region i1 may be set to an ROI, and the blocking units 132 to 135 (see FIG. 5) may be controlled such that radiation can be irradiated to the first region i1. If the target of interest moves from the first region i1 to the second region i2, the second region i2 may be set to a new ROI, and the blocking units 132 to 135 may be controlled such that radiation can be irradiated to the second region i2. More specifically, a part of the blocking elements 1321, 1331, 1341, and 1351 (see FIG. 5) may move in a right direction as shown in FIG. 8, and the other part of the blocking elements 1321, 1331, 1341, and 1351 may move in a up direction as shown in FIG. 8, thereby changing the ROI from the first region i1 to the second region i2.

Figure 9:
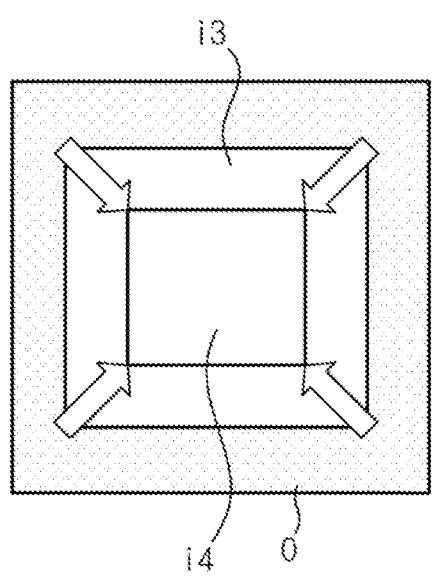

In FIG. 9, an example of reducing an ROI is shown. There is a case in which an ROI does not need to be set to a wide area because a target of interest inside an object ob is located in the center of the ROI. In this case, as shown in FIG. 9, the blocking units 132 to 135 may be controlled to reduce an ROI from the third region i3 having a relatively wide area to a fourth region i4. At this time, by approaching the blocking elements 1321, 1331, 1341, and 1351 toward the center of the corresponding radiographic image, the ROI can be reduced.

Figure 10:
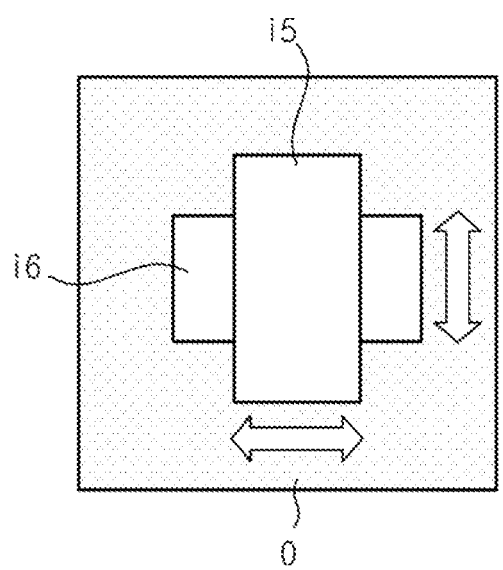

In FIG. 10, an example of adjusting a width of an ROI is shown. When the entire of a target of interest inside an object ob is not displayed or when a target of interest can be photographed only by changing the size of an ROI, the blocking units 132 to 135 may be controlled to change a width of a fifth region i1 or a sixth region i6 that is a set ROI, as shown in FIG. 10. In this case, by fixing a part of the blocking elements 1321, 1331, 1341, and 1351 and moving the other part of the blocking elements 1321, 1331, 1341, and 1351 in a direction away from the center of the corresponding radiographic image, a width of the fifth region i5 or the sixth region i6 may be adjusted.

Figure 11:
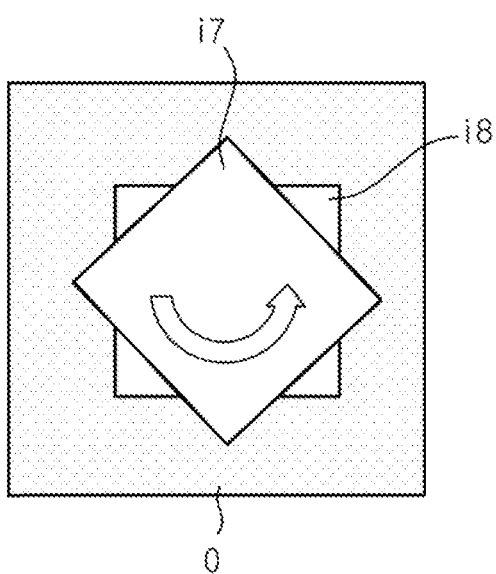

In FIG. 11, an example of rotating an ROI is shown. When there is a need to rotate an ROI, by rotating the blocking elements 1321, 1331, 1341, and 1351 with respect to a desired axis (that may or may not be predetermined), for example, with respect to a center point of the corresponding radiographic image, the ROI may be rotated. In FIG. 11, a seventh region i7 is an ROI before rotation, and an eighth region i8 is an ROI after rotation.

Figure 12:
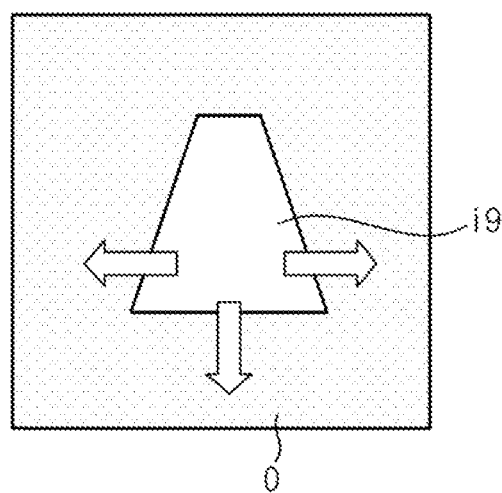

In FIG. 12, an example of setting an ROI in a shape of a trapezoid is shown. As shown in FIG. 12, an ROI i9 may be in a shape of a trapezoid, other than a square or a rectangle. In this case, by fixing a part of the blocking elements 1321, 1331, 1341, and 1351 and moving the remaining blocking elements away from the center of the corresponding image, the region i9 may be changed to a shape of a trapezoid. That is, by controlling the blocking units 132 to 135 in various methods, the position, shape, and size of an ROI may be adjusted.

Radiation irradiated from the radiation irradiator 111, except for a part of radiation corresponding to a desired region (that may or may not be predetermined), for example, an ROI, may be blocked by the irradiation zone adjustor 130. As such, if radiation is irradiated only to the desired region (that may or may not be predetermined) corresponding to an ROI, an amount of radiation that is irradiated to the object ob may be reduced, resulting in a reduction of a dose of radiation to which the object ob is exposed. If radiation is irradiated to the object ob, the inside tissue of the object ob may absorb a part of the radiation, and transmit the remaining part of the radiation, according to the properties of the inside tissue. The radiation transmitted through the object ob may be detected by the radiation detecting module 120.

According to some example embodiments, the radiation detecting module 120 may include a radiation detector 121, as shown in FIG. 2. The radiation detector 121 may receive radiation that is transmitted through the object ob or that arrives directly at the radiation detector 121 without passing through the object ob, convert the radiation into electrical signals, and output the electrical signals. According to some example embodiments, the radiation detector 121 may directly convert the radiation into electrical signals (direct method), or may generate visible light corresponding to the radiation and then convert the visible light into electrical signals (indirect method).

Figure 13:
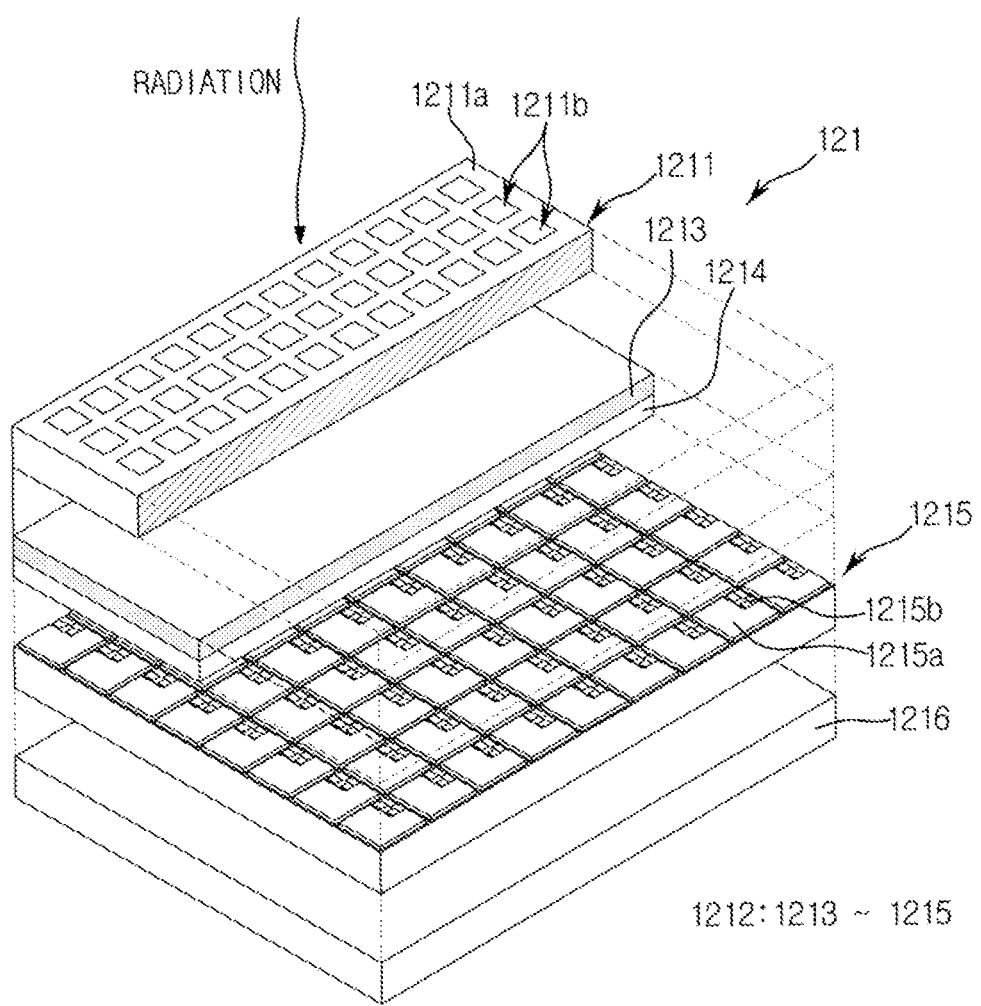
FIG. 13 is a perspective view of a radiation detector according to some example embodiments of the present disclosure.

FIG. 13 is a perspective view of the radiation detector 121 according to some example embodiments of the present disclosure.

If the radiation detector 121 converts the radiation into electrical signals according to the direct method, the radiation detector 121 may include a second collimator 1211, a radiation detecting panel 1212, and a board 1216, as shown in FIG. 13.

The second collimator 1211 may allow radiation traveling in a desired direction (that may or may not be predetermined) among radiation transmitted through the object ob to arrive at the radiation detecting panel 1212. When radiation passes through the object ob, the radiation may be deflected or scattered according to the properties and structure of the inside tissue of the object ob. The second collimator 1211 may filter the radiation deflected or scattered by the inside tissue of the object ob, and enable individual pixels of the radiation detecting panel 1212 to receive appropriate radiation.

The second collimator 1211 may include a partition wall 1211a to block radiation, and a plurality of transmission holes 1211b through which radiation is transmitted. The partition wall 1211a may be made of lead (Pb) capable of absorbing radiation in order to absorb radiation scattered or deflected. Radiation that has been neither scattered nor deflected may be transmitted through the transmission holes 1211b and arrive at the radiation detecting panel 1212.

The radiation detecting panel 1212 may include a first electrode 1213, whose one side radiation is incident to, a semiconductor material layer 1214 applied on the other side of the first electrode 1213 to which no radiation is incident, and a plane plate 1215 applied to a side of the semiconductor material layer 1214 that is opposite to the side of the semiconductor material layer 1214 on which the first electrode 1213 is applied. The plane plate 1215 applied on the semiconductor material layer 1214 may include a plurality of second electrodes 1215a and a plurality of thin film transistors 1215b. The first electrode 1213 may have positive (+) or negative (−) polarity, and the polarity of the second electrodes 1215a may be opposite to that of the first electrode 1213. Accordingly, if the first electrode 1213 is a positive (+) electrode, the polarity of the second electrodes 1215a may be negative (−). A desired bias voltage (that may or may not be predetermined) may be applied between the first electrode 1213 and the second electrodes 1215a.

The semiconductor material layer 1214 may create an electron-hole pairs according to transmission and absorption of radiation. The created electron-hole pairs may move toward the first electrode 1213 or the second electrodes 1215a according to the polarities of the first electrode 1213 and the second electrodes 1215a.

The second electrodes 1215a may receive holes or negative charges transmitted from the semiconductor material layer 1214. The holes or negative charges transmitted to the second electrodes 1215a may be stored in a desired storage device, for example, in a capacitor. Meanwhile, the second electrodes 1215a may be arranged in an array on the plane plate 1215. For example, the second electrodes 1215a may be arranged in a line or in a plurality of lines on the plane plate 1215.

The thin film transistors 1215b may read electrical signals transmitted from the second electrodes 1215a or stored in a the desired storage device. The thin film transistors 1215b may connect to the corresponding second electrodes 1215a so as to receive electrical signals from the second electrodes 1215a. Each second electrode 1215a and a thin film transistor 1215b corresponding to the second electrode 1215a may be mounted on a complimentary metal-oxide-semiconductor (CMOS) chip.

When the radiation detector 121 converts radiation into electrical signals according to the indirect method, a phosphor screen may be interposed between the second collimator 1211 and the radiation detecting panel 1212. The phosphor screen may receive radiation irradiated from the radiation irradiator 111, and output visible light corresponding to the received radiation. In this case, in order to receive the visible light, photodiodes, instead of the second electrodes 1215a, may be installed on the plane plate 1215. The photodiodes may be arranged in a line or in a plurality of lines, like the second electrodes 1215a.

According to some example embodiments, the radiation detecting panel 1212 may further include a scintillator to receive radiation and to output visible photons according to the received radiation, and photodiodes to sense the visible photons output from the scintillator. The photodiodes may output electrical signals, for example, electrical charge packets consisting of holes or negative charges, according to the visible photons. The electrical charge packets may be stored in a desired storage device, for example, in a capacitor.

Meanwhile, according to some example embodiments, the radiation detector 121 may be a photon counting detector (PCD). The PCD may count photons having higher energy than threshold energy from radiation signals so as to acquire measurement data. The PCD may amplify received radiation signals, compare the amplified electrical signals to threshold energy to determine whether the amplified electrical signals have energy that is higher than the threshold energy, and count photons having energy that is higher than the threshold energy according to the results of the comparison to measure an intensity of radiation. The PCD may adjust the threshold energy that is compared to the amplified electrical signals to detect radiation of a desired energy spectrum (that may or may not be predetermined).

The board 1216 may be attached on the other side of the radiation detecting panel 1212. The board 1216 may be configured to control various operations of the radiation detecting panel 1212.

Electrical signals acquired by the radiation detector 121 may be raw data for a radiographic image. The electrical signals may be transferred to an image processor 220 of FIG. 2. The image processor 220 may produce a radiographic image based on electrical signals acquired by the radiation detector 121.

The radiographic apparatus 1 may further include the cradle 161 on which an object ob can be placed, between the radiation irradiating module 110 and the radiation detecting module 120, as shown in FIG. 1. The cradle 161 may be a table on which an object ob can be placed, however, an external appearance of the cradle 161 is not limited to this. That is, the cradle 161 may have one of various shapes that one of ordinary skill in the art can consider. According to some example embodiments, the cradle 161 may convey the object ob placed thereon in a desired direction (that may or may not be predetermined). In this case, the cradle 161 may include various conveying means, such as a motor, a wheel, or a rail, to move a part on which the object ob is placed.

The radiographic apparatus 1 may include, as shown in FIG. 2, a workstation 200. The workstation 200 may include the controller 210 and the image processor 220. In FIG. 2, an example in which the workstation 200 includes the controller 210 and the image processor 220 is shown. However, the workstation 200 may not necessarily include the controller 210 and the image processor 220. The controller 210 and the image processor 220 may be included in another device than the workstation 200. For example, the radiographic module 100 may include the controller 210 and the image processor 220.

The controller 210 may control overall operations of the radiographic apparatus 1. The controller 210 may control operations of the radiation irradiating module 110 and the radiation detecting module 120. For example, the controller 210 may cause the radiation irradiator 111 to start or stop irradiating radiation of a desired energy spectrum (that may or may not be predetermined), or cause the irradiation zone adjustor 130 to adjust an irradiation zone. Also, the controller 210 may control driving of the radiography module driver 140, for example, the C-arm module 140*a* (see FIG. 1). More specifically, the controller 210 may generate and transmit appropriate control signals to control the first frame 142*a*, the second frame 142*b*, the third frame 143, the first rotating unit 141, the second rotating unit 145, and the horizontal movement unit 144 of the radiography module driver 140, for example, the C-arm module 140*a* (see FIG. 3).

The controller 210 may generate control signals for driving the radiation irradiating module 110, the radiation detecting module 120, and the radiography module driver 140 according to desired settings (that may or may not be predetermined). The desired settings (that may or may not be predetermined) may be stored in a storage device installed in the radiographic module 100 or in the workstation 200. Also, the controller 210 may interpret a user's instruction or command received through an input unit 300 provided in the radiographic module 100 or the workstation 200, and generate a control signal according to the result of the interpretation to control operations of the radiation irradiating module 110, the radiation detecting module 120, and the radiography module driver 140.

According to some example embodiments, the controller 210 may automatically set a part of a region over which the radiation irradiator 111 can irradiate radiation to an ROI. In this case, according to some example embodiments, the controller 210 may automatically set an ROI for a radiographic image at regular time intervals, without a user having to manually set an ROI. Also, the controller 210 may automatically set an ROI for each radiographic image whenever the radiation irradiating module 110 irradiates radiation to an object ob.

Figure 14:
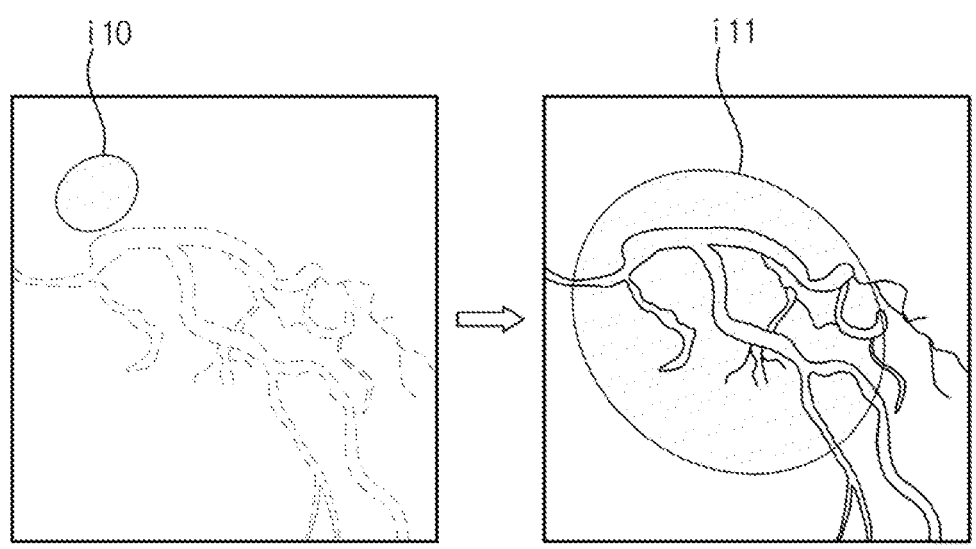
FIGS. 14 and 15 are views for describing various examples of images that are displayed on screens when ROIs change.
Figure 15:
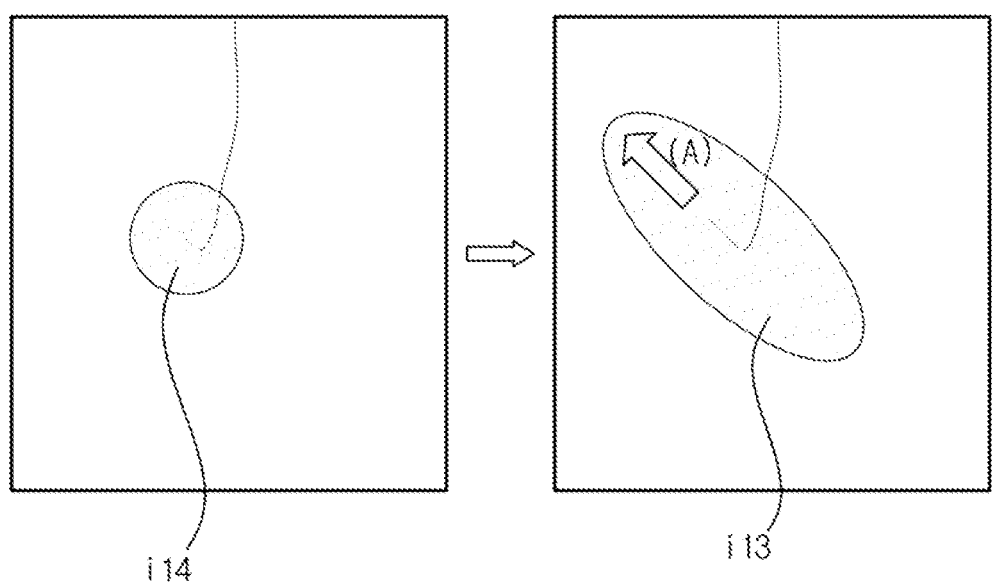

FIGS. 14 and 15 are views for describing various examples of images that are displayed on screens when ROIs change.

As shown in FIG. 14, if a desired ROI i10 (that may or may not be predetermined) does not include a region which an operator wants to see, for example, a region in which blood vessels are distributed, the controller 210 may automatically extend the ROI i10 to set a new ROI i11.

As shown in FIG. 15, if a contrast agent moves along a blood vessel, the controller 210 may automatically predict a movement path of the contrast agent to extend the desired ROI i12 (that may or may not be predetermined) in a desired direction A (that may or may not be predetermined) and set a new ROI i13. As such, if an ROI is automatically set, it is possible to adjust an irradiation amount of radiation to a required amount, resulting in a reduction of a dose of radiation to which the object ob is exposed.

According to some example embodiments, the controller 210 may estimate a new ROI based on a desired ROI (that may or may not be predetermined). In this case, the desired ROI (that may or may not be predetermined) may be an initial value of an ROI. The initial value of the ROI may be set manually by a user or automatically according to desired settings (that may or may not be predetermined). For example, the controller 210 may estimate a new ROI based on the desired ROI (that may or may not be predetermined), using Kalman filtering (Linear Quadratic Estimation (LQE)), and automatically set the new ROI.

The Kalman filter is an algorithm useful to estimate a value at a specific time based on a value measured or estimated at a previous time. The Kalman filter may estimate a value at a specific time from a value measured or estimated at the previous time according to a recursive method. The value measured or estimated at the previous time may include error. Accordingly, the Kalman filter is used to acquire a more accurate value than that acquired through measurement. More specifically, the Kalman filter may estimate a value at a specific time through prediction and update. The Kalman filter may calculate a predicted value (hereinafter, referred to as a predicted value related to a location of an ROI) regarding an estimated value for a location of an ROI, and a predicted value (hereinafter, referred to as a predicted value related to covariance) regarding an estimated value for covariance representing an error of the location of the ROI (prediction); and acquire a predicted value related to the location of the ROI and a predicted value related to covariance, using a measured value for the location of the ROI, detected from a radiographic image (update). Accordingly, the controller 210 may trace and determine the location of the ROI. If the location of the ROI is determined, an ROI for which a radiographic image will be acquired may be determined according to the location of the ROI.

Figure 16:
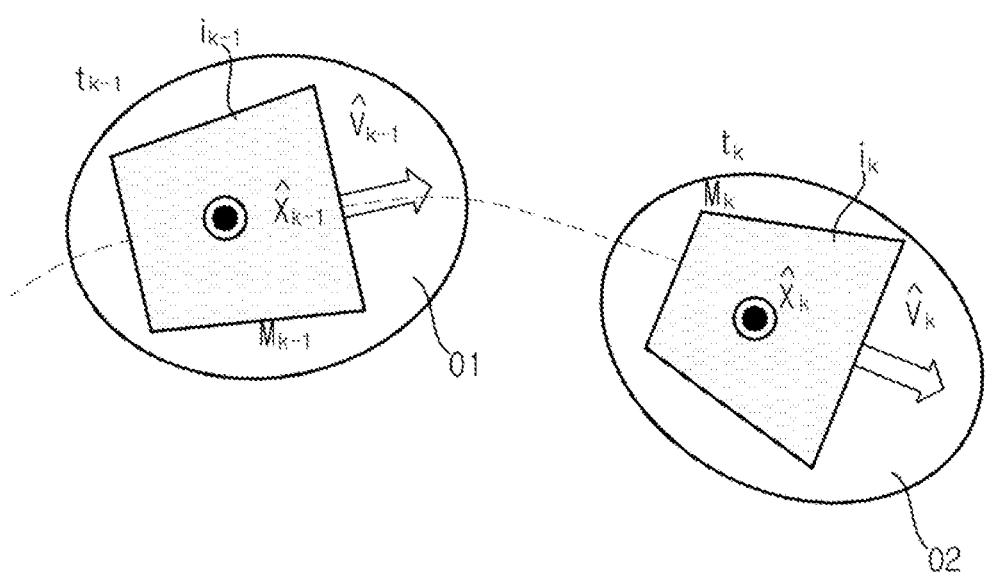
FIG. 16 is a view for describing a method of setting an ROI using Kalman filtering according to some example embodiments of the present disclosure.

FIG. 16 is a view for describing a method of tracking an ROI using Kalman filtering according to some example embodiments of the present disclosure.

In FIG. 16, $t_{k-1}$ and $t_k$ represent times at which a location of an ROI is measured or estimated, and $x_{k-1}$ and $x_k$ represent the locations of the ROI measured or estimated at the respective times $t_{k-1}$ and $t_k$. $v_{k-1}$ and $v_k$ represent velocities of a target of interest at the respective times $t_{k-1}$ and $t_k$, and $M_{k-1}$ and $M_k$ represent operations of the irradiation zone adjustor 130 at the respective times $t_{k-1}$ and $t_k$. $i_{k-1}$ and $i_k$ represent ROIs at the respective times $t_{k-1}$ and $t_k$. Meanwhile, a hat over an alphabetic character means that a value corresponding to the alphabetic character is an estimated value. Also, 01 and 02 represent zones of images that can be acquired when the blocking units 132 to 135 of the irradiation zone adjustor 130 do not block any irradiated radiation. In this case, an estimated value related to a location of an ROI may be calculated according to Equation 2 below, and an estimated value related to covariance representing an error value of the location of the ROI may be calculated according to Equation (3) below.

$$\hat{X}_k^- = F\hat{X}_{k-1}, \text{ and} \quad (2)$$

$$\hat{P}_k^- = F\hat{P}_{k-1}F^T + Q. \quad (3)$$

In Equations (3) and (4), X represents the location of the ROI, $\hat{X}$ represents an estimated value related to the location of the ROI, P represents covariance representing an error value of the location of the ROI, and $\hat{P}$ represents an estimated value of the covariance representing the error value of the location of the ROI. Meanwhile, $X^-$ and $P^-$ represent estimated values for X and P. F represents state-transition transform based on the previous state at a specific time ($F^T$ is the transform of F), and Q represents process covariance. As shown in Equations (2) and (3), an estimated value related to the location of the ROI and an estimated value related to covariance may be recursively calculated. If an estimated value related to the location of the ROI and an estimated value related to covariance are calculated, a predicted value related to the location of the ROI and a predicted value related to covariance may be acquired using a measured value for the location of the ROI. In this case, Kalman gain may be first calculated. The Kalman gain may be used as a weight value corresponding to a difference between the measured value and the estimated value.

Kalman gain may be calculated using Equation 4 below.

$$K_k = \hat{P}_k^- H^T (H\hat{P}_k^- H^T + R), \quad (4)$$

where $K_k$ represents Kalman gain, R represents measured covariance, and H represents a value related to measurement at a specific time ($H^T$ is the transform of H).

If Kalman gain is calculated by Equation (4), the estimated value related to the location of the ROI and the estimated value related to covariance may be updated using the Kalman gain. A updated value for the estimated value related to the location of the ROI may be calculated using Equation (5) below, and a updated value for the estimated value related to the covariance representing the error value of the location of the ROI may be calculated using Equation (6) below.

$$\hat{X}_k = \hat{X}_k^- + K_k(Y_k - H\hat{X}_k^-), \text{ and} \quad (5)$$

$$\hat{P}_k = (I - K_k H)\hat{P}_k^-. \quad (6)$$

In Equation (5), $Y_k$ represents the measured value for the location of the ROI, detected from a radiographic image. In Equation (6), I represents a unit (identity) matrix. The remaining symbols have been described above. The updated value calculated by Equation (5) may be a predicted value for the location of the ROI, and the updated value calculated by Equation (6) may be a predicted value for the covariance representing the error value of the location of the ROI. Accordingly, it is possible to estimate a location of an ROI and to ensure a confidence limit of the estimated value.

If the location of the ROI is estimated, the controller 210 may set a new ROI according to the location of the ROI. According to some example embodiments, the controller 210 may calculate an estimated value for the location of the ROI and an estimated value for covariance representing an error value of the location of the ROI, and then a user may input corrected values for the respective estimated values. The controller 210 may reflect the corrected values received from the user to the respective estimated values, and then set a new ROI according to the results of the reflection.

If a new ROI is set, the controller 210 may determine a radiation irradiation position and a radiation irradiation zone of the radiation irradiating module 110, according to the new ROI. Successively, the controller 210 may generate control signals corresponding to the radiation irradiation position and the radiation irradiation zone according to the results of the determination. For example, the controller 210 may generate control signals for moving the radiation irradiating module 110 and the radiation detecting module 120, or a control signal for adjusting the irradiation zone adjustor 130. The generated control signals may be transferred to the radiation irradiating module 110, the radiation detecting module 120, and/or the radiography module driver 140.

The radiation irradiating module 110, the radiation detecting module 120, and/or the radiography module driver 140 may be controlled according to a control signal(s) received from the controller 210. According to some example embodiments, the radiography module driver 140 may move the radiation irradiating module 110 and the radiation detecting module 120 according to a radiation irradiation position determined by the controller 210, based on control signals received from the controller 210. According to some example embodiments, the radiography module driver 140 may drive the irradiation zone adjustor 130 of the radiation irradiating module 110 to adjust a radiation irradiation position and a radiation irradiation zone according to determinations by the controller 210. Any one or all of movements of the radiation irradiating module 110 and the radiation detecting module 120, and irradiation zone adjustment by the irradiation zone adjustor 130, may be performed. When all of movements of the radiation irradiating module 110 and the radiation detecting module 120 and irradiation zone adjustment by the irradiation zone adjustor 130 are performed, the movements of the radiation irradiating module 110 and the radiation detecting module 120 and the irradiation zone adjustment by the irradiation zone adjustor 130 may be performed at the same time or at different times.

The radiation irradiating module 110 may irradiate radiation to the object ob according to the radiation irradiation position and the radiation irradiation zone determined by the controller 210. The radiation detecting module 120 may receive radiation transmitted through the object ob, and convert the radiation into electrical signals. The image processor 220 may produce a radiographic image based on the electrical signals. As a result, a radiographic image for the set ROI may be acquired.

The image processor 220 may reconstruct and produce a radiographic image based on raw data transferred from the radiation detector 121. The image processor 220 may produce a radiographic image for the entire region or for an ROI. According to some example embodiments, the image processor 220 may combine a radiographic image acquired in advance with a radiographic image for an ROI to produce a combined image. The radiographic image acquired in advance may be a radiographic image including the ROI. More specifically, the image processor 220 may detect features points from the radiographic image acquired in advance and the radiographic image for the ROI, and match the detected feature points with respect to the radiographic image acquired in advance and the radiographic image for the ROI, thereby combining the radiographic image for the entire region with the radiographic image for the ROI. According to some example embodiments, the image processor 220 may perform post-processing on the reconstructed radiographic image. For example, the image processor 220 may correct luminosity, brightness, contrast, and sharpness with respect to the entire or a part of the radiographic image. The image processor 220 may correct the reconstructed radiographic image according to a user's instruction or command received through the input unit 300 or according to desired settings (that may or may not be predetermined).

The controller 210 and the image processor 220 may be processors. The processor may include a semiconductor chip for performing various operations, processing, and storing, and various circuitry. The processor may be a Central Processing Unit (CPU) or a microprocessor. The controller 210 and the image processor 220 may be implemented as a single processor or as separate processors. As necessary, the image processor 220 may be implemented as a Graphics Processing Unit (GPU). The processor and the GPU may each include a semiconductor chip and various circuitry.

The radiographic apparatus 1 may further include, as shown in FIG. 2, the input unit 300 to receive a desired instruction or command (that may or may not be predetermined) from a user. According to some example embodiments, the input unit 300 may receive a desired instruction (that may or may not be predetermined) for changing a radiation irradiation position and a radiation irradiation zone determined by the controller 210. For example, the input unit 300 may include, for example, a keyboard, a mouse, a track-ball, a touch screen, a touch pad, a paddle, various kinds of levers, a handle, a joystick, or various input devices. The input unit 300 may be one of the above-mentioned devices, or a combination of two or more of the above-mentioned devices. According to some example embodiments, the input unit 300 may be mounted on the radiographic module 100. For example, the input unit 300 may be provided on the external housing of the radiation irradiating module 110. As another example, the input unit 300 may be connected to the workstation 200 in a wired or wireless fashion.

The radiographic apparatus 1 may further include, as shown in FIGS. 1 and 2, a display unit 400 to display a desired image (that may or may not be predetermined). The display unit 400 may be connected to the radiographic module 100, or connected to the workstation 200 in a wired or wireless fashion.

The display unit 400 may display a produced radiographic image, various information about the radiographic image, a Graphical User Interface (GUI) for various information and various instructions or commands required for radiography, or various information that can be displayed. According to some example embodiments, the display unit 400 may display an ROI of a radiographic image. In this case, the display unit 400 may partition a radiographic image with desired lines (that may or may not be predetermined) or a desired curved line (that may or may not be predetermined) to display an ROI. Also, the display unit 400 may display an image for an ROI before the ROI is newly set, a newly set ROI, change details of the ROI, a radiographic image for the newly set ROI, or a combined radiographic image. According to some example embodiments, the display unit 400 may be a touch screen and, in this case, the display unit 400 may also function as the input unit 300.

As an example of an apparatus capable of quickly and accurately setting and tracing an ROI, a radiographic apparatus has been described, however, such an apparatus is not limited to a radiographic apparatus. The apparatus may be applied to various apparatuses required to quickly trace an ROI. For example, an industrial robot may be an example of an apparatus capable of quickly and accurately setting and tracing an ROI.

Hereafter, some example embodiments of a method of setting an ROI will be described with reference to FIG. 17.

In the following description, a method of setting an ROI using the radiographic apparatus 1 will be given as an example. However, the method of setting the ROI may be applied to any other imaging apparatus including a device capable of adjusting a photographing position and a photographing zone at the same time or at different times, in the same way as in the radiographic apparatus 1 or in a partially modified way.

Figure 17:
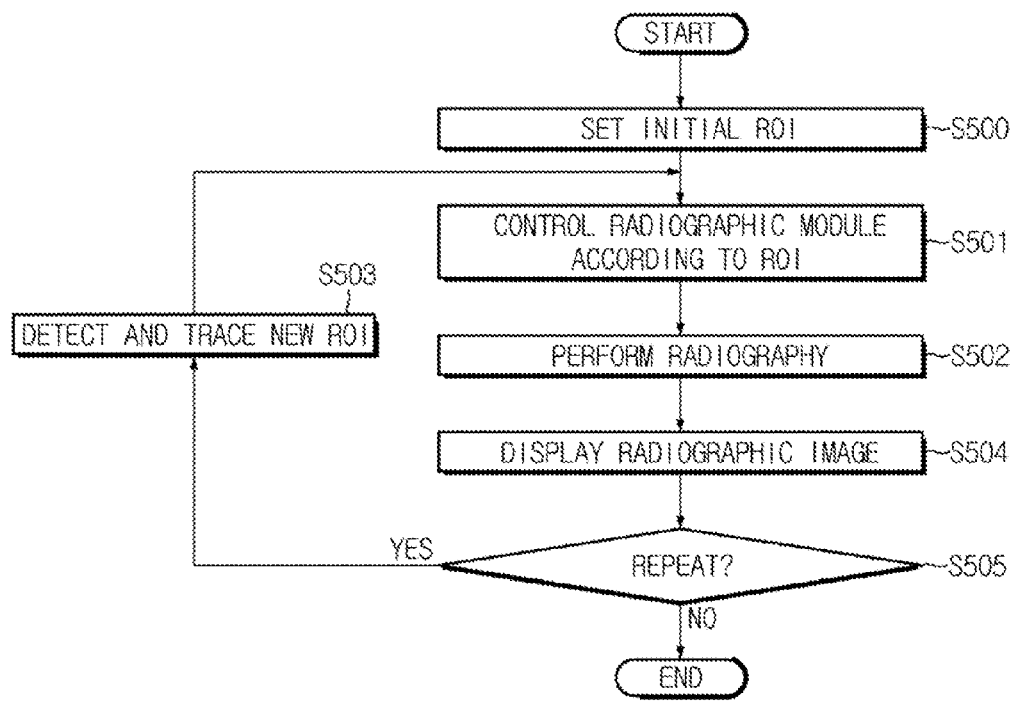
FIG. 17 is a flowchart illustrating a method of tracing an ROI, according to some example embodiments of the present disclosure.

Referring to FIGS. 1, 2, and 17, first, an initial ROI may be set, in operation S500. The initial ROI may be set by a user or according to a desired setting (that may or may not be predetermined). The initial ROI may depend on a kind of a procedure. For example, in a radiographic apparatus, the initial ROI may be set automatically or manually according to a kind of surgical operation or diagnosis.

If an initial ROI is set, a radiation irradiation position and a radiation irradiation zone may be determined according to the initial ROI. If a radiation irradiation position and a radiation irradiation zone are determined, the radiographic module 100 may be controlled to acquire a radiographic image corresponding to the ROI, in operation S501.

In order for the radiographic module 100 to perform radiography according to the radiation irradiation position and the radiation irradiation zone, the radiation irradiating module 110 and the radiation detecting module 120 may move, and/or the irradiation zone adjustor 130 may be adjusted. All of movements of the radiation irradiating module 110 and the radiation detecting module 120, and driving of the irradiation zone adjustor 130 may be performed. In this case, the movements of the radiation irradiating module 110 and the radiation detecting module 120, and the driving of the irradiation zone adjustor 130, may be performed at the same time or at different times. The radiation irradiating module 110 and the radiation detecting module 120 may be linearly moved or rotated in a desired direction (that may or may not be predetermined) by the radiography module driver 140, for example, by the C-arm module 140a. The irradiation zone adjustor 130 may adjust a radiation irradiation position and a radiation irradiation zone by moving the blocking units 132 to 135 (see FIG. 5) to desired positions (that may or may not be predetermined).

If the radiographic module 100 is appropriately controlled, the radiographic module 100 may perform radiography so that a radiographic image is acquired, in operation S502. The radiographic image may be a radiographic image for an ROI.

The radiographic image acquired in operation S502 may be displayed through the display unit 400 for a user, in operation S504. In this case, the radiographic image may be a radiographic image of an ROI, or a radiographic image resulting from combining a radiographic image of an ROI with a radiographic image acquired in advance.

After the radiographic image is displayed, there may be a need to set a new ROI or to change the ROI. For example, the initial ROI may not be an ROI which the user wants to see. Also, due to movement of a target of interest displayed on the radiographic image, the ROI may change. As such, when there is a need to change the set ROI, the radiographic apparatus 1 may automatically determine and trace a new ROI, in operations S503 and S505. A new ROI may be determined based on the set ROI. According to some example embodiments, a new ROI may be determined based on the set ROI using Kalman filtering. If a new ROI is determined in operation S503, operation S501 of controlling the radiographic module 100, operation S502 of performing radiography, and operation S504 of displaying a radiographic image may be repeatedly performed. In this case, operation S501 of controlling the radiographic module 100 may be performed based on the newly determined ROI. Likewise, in order for the radiographic module 100 to perform radiography according to the newly determined ROI, the radiation irradiating module 110 and the radiation detecting module 120 may move, or the irradiation zone adjustor 130 may be adjusted, in operation S501, and successively, operation S502 of performing radiography and operation S504 of displaying a radiographic image may be performed.

The method of FIG. 17 may be used in more general purpose systems and/or for methods of controlling such systems. For example, the method may be used in autonomous devices and/or for controlling such devices so as to allow operation of the autonomous devices.

Hereinafter, a method of controlling the radiographic apparatus 1, according to some example embodiments of the present disclosure, will be described with reference to FIG. 18.

Figure 18:
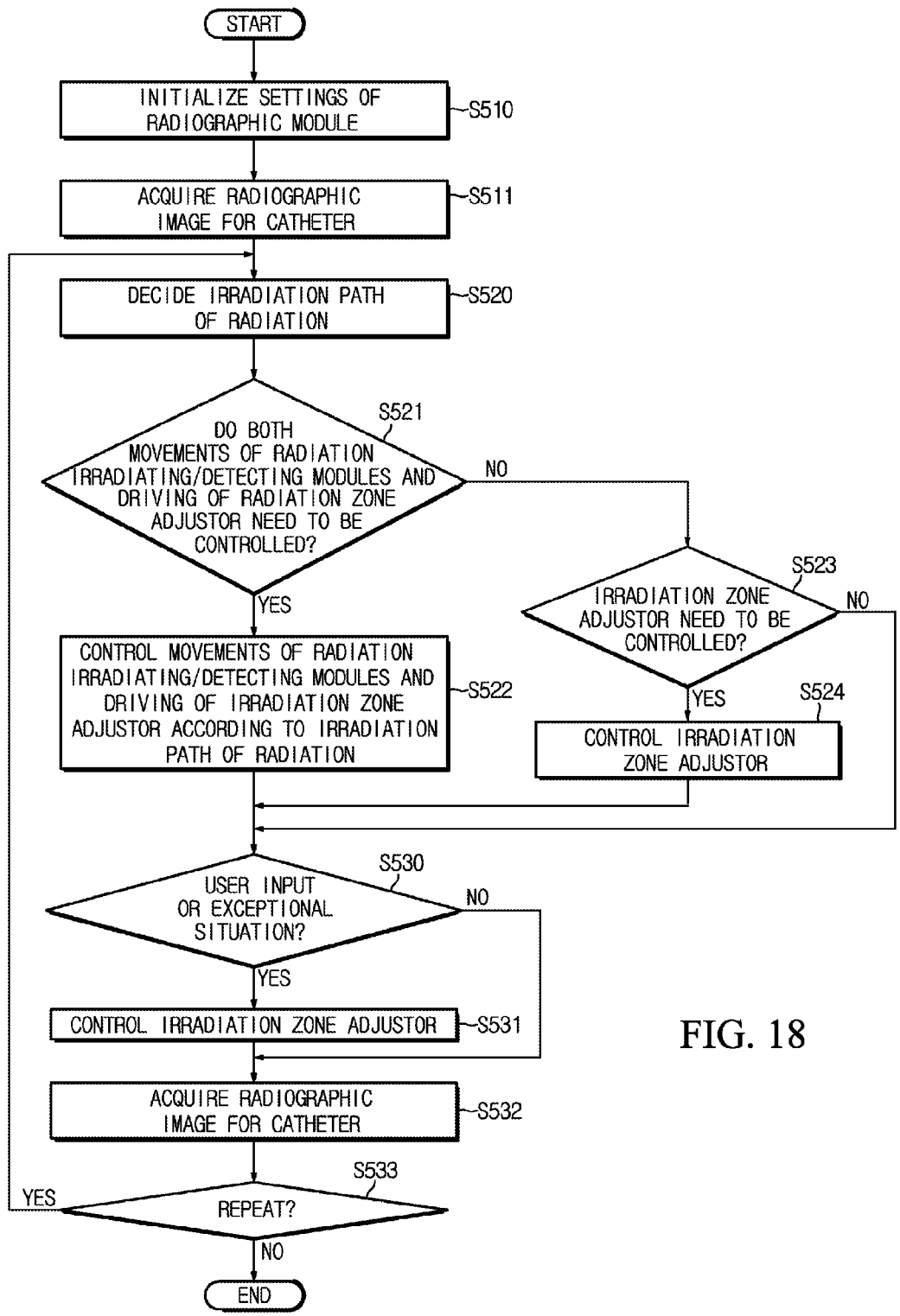
FIG. 18 is a flowchart illustrating a method of controlling a radiographic apparatus according to some example embodiments of the present disclosure.

The method of controlling the radiographic apparatus 1, as shown in FIG. 18, relates to a method of controlling the radiographic apparatus 1 to trace an ROI when a catheter is a target of interest. Referring to FIGS. 1, 2, and 18, settings of the radiographic module 100 (the movements of the radiation irradiating module 110 and the radiation detecting module 120, and the driving of the irradiation zone adjustor 130) may be initialized in order to photograph a desired region (that may or may not be predetermined), in operation S510, and a radiographic image for the catheter may be acquired according to the initialized settings of radiographic module 100, in operation S511. The acquired radiographic image may be a radiographic image for an initialized, desired ROI (that may or may not be predetermined), or for the entire region on which radiography can be performed, regardless of an ROI. A radiographic image for the entire region on which radiography can be performed may be combined with a radiographic image for an ROI. As necessary, in operations S510 and S511, both a radiographic image for an initialized ROI and a radiographic image for the entire region may be acquired.

If a radiographic image is acquired, an ROI may be automatically set based on the radiographic image. A radiation irradiation position and a radiation irradiation zone, which decide an irradiation path of radiation, may be determined based on the ROI, in operation S520. For example, if the catheter disappears from the radiographic image, an ROI may be set in such a manner to move a location of the ROI in the movement direction of the catheter or to widen the area of the ROI. According to some example embodiments, an ROI may be set using a desired ROI (that may or may not be predetermined), for example, an initial value of an ROI. More specifically, an ROI may be set using an algorithm based on a recursive method such as Kalman filtering.

If a radiation irradiation position and a radiation irradiation zone that decide an irradiation path of radiation are determined, it may be determined whether to control the radiographic module 100. Specifically, it may be determined whether both the movements of the radiation irradiating module 110 and/or the radiation detecting module 120, and the driving of the irradiation zone adjustor 130, have to be controlled, in operation S521.

If there is a need to adjust a radiation irradiation zone while moving the radiation irradiating module 110 and/or the radiation detecting module 120 according to the decided irradiation path of radiation, the radiation irradiating module 110, the radiation detecting module 120, and/or the irradiation zone adjustor 130 may be controlled, in operation S522. In this case, the radiation irradiating module 110 and/or the radiation detecting module 120 may be moved by the radiography module driver 140, and the blocking units 132 to 135 (see FIG. 5) of the irradiation zone adjustor 130 may move to change the radiation irradiation zone and the radiation irradiation position.

If only adjusting a radiation irradiation zone is needed without having to move the radiation irradiating module 110 and/or the radiation detecting module 120, in operation S523, although the catheter disappears from the radiographic image, as shown in FIGS. 15 and 16, a radiation irradiation zone and a radiation irradiation position may be changed by adjusting the irradiation zone adjustor 130, in operation S524.

If it is determined that there is no need to control the radiographic module 100, based on the decided irradiation path of radiation, the radiographic module 100 is not controlled.

Meanwhile, according to some example embodiments, after the radiographic module 100 is controlled or not controlled, a desired instruction or command (that may or may not be predetermined) for controlling the radiographic module 100 may be received from a user, in operation S530. If a desired instruction or command (that may or may not be predetermined) for controlling the radiographic module 100 is received from a user, the radiographic module 100 may be controlled according to the instruction or command from the user. According to the instruction or command from the user, a radiation irradiation position and a radiation irradiation zone may be more finely adjusted by the irradiation zone adjustor 130, in operation S531. Although no desired instruction (or command) (that may or may not be predetermined) from a user is received, the irradiation zone adjustor 130 may be automatically controlled when an exceptional situation (that may or may not be predetermined) occurs, also in operation S531.

After the radiographic module 100 is controlled based on a radiation irradiation position and a radiation irradiation zone determined according to an ROI, in other words, after the radiation irradiating module 110 and the irradiation zone adjustor 130 are moved or adjusted, the radiation irradiating module 110 may irradiate radiation to an object ob. Then, the radiation detecting module 120 may receive radiation transmitted through the object ob to again acquire a radiographic image for the catheter, in operation S532.

Operations S520 to S532 may be automatically performed by the radiographic apparatus 1. Also, operations S520 to S532 may be repeatedly performed. Operations S520 to S532 may be repeated per a desired time period (that may or may not be predetermined), in operation S533.

The method of FIG. 18 may be used in more general purpose systems and/or for methods of controlling such systems. For example, the method may be used in intelligent robots and/or for controlling such devices so as to allow safe operation of the intelligent robots.

Therefore, according to the method of tracing the ROI, the radiographic apparatus, the control method of the radiographic apparatus, and the radiography method, as described above, it is possible to quickly and accurately set and trace an ROI.

According to the radiographic apparatus and the control method of the radiographic apparatus, it is possible to reduce a dose of radiation to which an object is exposed during radiography.

Also, according to the method of tracing the ROI, the radiographic apparatus, and the control method of the radiographic apparatus, as described above, since an image for an optimal ROI can be acquired quickly or in real time, operation such as surgery can be unremittedly performed.

Furthermore, when the method of tracing the ROI, the radiographic apparatus, and the control method of the radiographic apparatus, as described above, are applied to brain surgery, it is possible to provide an operator with information about the progress of surgery and various information related to surgery in real time.

In addition, according to the method of tracing the ROI, as described above, an intelligent robot, etc. can quickly recognize an object to perform desired operation.

The algorithms discussed in this application (e.g., required to control the radiographic apparatuses and methods) may be used in more general purpose apparatuses and/or methods of controlling apparatuses. For example, the algorithms may be used in intelligent robots for handling equipment and materials and/or for controlling such intelligent robot so as to allow safe movement, packaging, and/or shipment of the equipment and materials.

The methods described above may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' may be interpreted as software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiment, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to radiographic apparatuses and methods, those skilled in the art will appreciate that some example embodiments may be applied to other types of systems and methods, such as systems not used in the medical field (e.g., aerospace teleoperation systems and methods, apparatuses and methods for handling hazardous materials, patrol apparatuses and methods, military apparatuses and methods), humanoid apparatuses and methods, or more general purpose control systems and methods. Those skilled in the art will appreciate that the radiographic apparatuses and methods described in this application have a myriad of practical uses.

Although some example embodiments of the present disclosure have been shown and described, it would be appreciated by those skilled in the art that changes may be made in these example embodiments without departing from the principles and spirit of the disclosure, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A radiographic apparatus, comprising:
   a radiation irradiator configured to irradiate radiation to an object;
   a radiography module driver configured to move or rotate the radiation irradiator;
   an irradiation zone adjustor configured to block a part of the irradiated radiation, wherein the irradiation zone adjustor includes a plurality of blocking elements and a plurality of blocking element drivers configured to move or rotate the plurality of blocking elements, respectively; and
   a controller configured to,
      automatically set a part of a region, to which the radiation irradiator is able to irradiate the radiation, to a region of interest,
      estimate a new region of interest based on the region of interest and a predicted movement path of a target of interest within the object,
      automatically determine a radiation irradiation position and a radiation irradiation zone based on the estimated new region of interest,
      send a first control signal to the radiography module driver to move or rotate the radiation irradiator according to the automatically determined radiation irradiation position and radiation irradiation zone, and
      send a second control signal to the irradiation zone adjustor to adjust at least one of the plurality of blocking elements, wherein one or more of the plurality of blocking element drivers move or rotate the one or more of the plurality of blocking elements so as to block the part of the irradiated radiation, according to the automatically determined radiation irradiation position and radiation irradiation zone,
   wherein the radiography module driver moves or rotates the radiation irradiator at a same time as the one or more of the plurality of blocking element drivers move or rotate the one or more of the plurality of blocking elements.

2. The radiographic apparatus according to claim 1, wherein the radiation irradiator is configured to irradiate radiation to the object according to the automatically determined radiation irradiation position and radiation irradiation zone.

3. The radiographic apparatus according to claim 2, further comprising:
   a radiation detector configured to receive the radiation transmitted through the object; and
   an image processor configured to produce a radiographic image of the region of interest that corresponds to the radiation received by the radiation detector.

4. The radiographic apparatus according to claim 3, wherein the image processor is further configured to combine the radiographic image of the region of interest with another radiographic image acquired in advance to produce a combined radiographic image.

5. The radiographic apparatus according to claim 3, wherein the controller is further configured to automatically set a part of the produced radiographic image to the estimated new region of interest using Kalman filtering.

6. The radiographic apparatus according to claim 1, wherein the radiography module driver comprises a C-arm module including the radiation irradiator.

7. The radiographic apparatus according to claim 1, wherein the controller is further configured to,
   automatically set the region of interest whenever the radiation irradiator irradiates radiation, and
   automatically determine the radiation irradiation position and the radiation irradiation zone whenever the region of interest is automatically set.

8. The radiographic apparatus according to claim 1, wherein the controller is further configured to automatically determine the radiation irradiation position and the radiation irradiation zone at regular time intervals.

9. A control method of a radiographic apparatus, the control method comprising:
   automatically setting a part of a region, to which radiation is to be irradiated, to a region of interest;
   estimating a new region of interest based on the region of interest and a predicted movement path of a target of interest within the object,
   automatically determining a radiation irradiation position and a radiation irradiation zone based on the estimated new region of interest;
   controlling a radiation irradiator and an irradiation zone adjustor based on the automatically determined the radiation irradiation position and radiation irradiation zone, wherein the controlling includes,
      sending a first control signal to a radiography module driver to control moving or rotating the radiation irradiator based on the automatically determined radiation irradiation position and radiation irradiation zone, and
      sending a second control signal to the irradiation zone adjustor to control adjusting at least one of a plurality of blocking elements, wherein one or more of a plurality of blocking element drivers move or rotate the one or more of the plurality of blocking elements so as to block a part of the irradiated radiation, based on the automatically determined radiation irradiation position and radiation irradiation zone;
   wherein the radiography module driver moves or rotates the radiation irradiator at a same time as the one or more of the plurality of blocking element drivers move or rotate the one or more of the plurality of blocking elements; and performing radiography according to the automatically determined radiation irradiation position and radiation irradiation zone to acquire a radiographic image of the estimated new region of interest.

10. The control method according to claim 9, further comprising:
   combining a radiographic image of the region of interest with another radiographic image acquired in advance to produce a combined radiographic image.

* * * * *